US009155669B2

(12) United States Patent
Petersen et al.

(10) Patent No.: US 9,155,669 B2
(45) Date of Patent: Oct. 13, 2015

(54) FASTENING FILM SYSTEM AND ASSEMBLY COMPRISING A FASTENING FILM SYSTEM AND A SUBSTRATE

(75) Inventors: Johann F. Petersen, Grevenbroich (DE); Ralf G. Oertel, Neuss (DE)

(73) Assignee: 3M Innovative Properties Company, St. Paul, MN (US)

( * ) Notice: Subject to any disclaimer, the term of this patent is extended or adjusted under 35 U.S.C. 154(b) by 1122 days.

(21) Appl. No.: 10/557,134

(22) PCT Filed: May 10, 2004

(86) PCT No.: PCT/US2004/014617
§ 371 (c)(1),
(2), (4) Date: Nov. 17, 2005

(87) PCT Pub. No.: WO2005/000180
PCT Pub. Date: Jan. 6, 2005

(65) Prior Publication Data
US 2007/0039142 A1 Feb. 22, 2007

(30) Foreign Application Priority Data
Jun. 6, 2003 (EP) .................................. 03012950

(51) Int. Cl.
*A61F 13/15* (2006.01)
*A61F 13/58* (2006.01)
(Continued)

(52) U.S. Cl.
CPC .............. *A61F 13/581* (2013.01); *Y10T 24/275* (2015.01); *Y10T 24/2758* (2015.01)

(58) Field of Classification Search
CPC ........... A61F 13/15; A61F 13/20; B31B 1/26; B31B 1/14; B31B 1/64; B31B 49/04
USPC ............ 604/386, 389, 385.13, 387, 391, 393, 604/394, 396, 400; 493/231, 373, 194; 156/160, 444, 66
See application file for complete search history.

(56) References Cited

U.S. PATENT DOCUMENTS

| 3,937,221 A | 2/1976 | Tritsch |
| 4,001,366 A | 1/1977 | Brumlik |

(Continued)

FOREIGN PATENT DOCUMENTS

| EP | 0374730 | 4/1994 |
| EP | 0418951 | 7/1995 |

(Continued)

OTHER PUBLICATIONS

Avery Brief, dated Apr. 29, 2013, pp. 1-25.
(Continued)

*Primary Examiner* — Tatyana Zalukaeva
*Assistant Examiner* — Ilya Treyger

(57) ABSTRACT

An assembly having a substrate bearing an adhesive layer having an extension in a machine direction and an extension in a cross-direction and a number of discrete portions of a backing, each discrete portion having a first major surface bearing a plurality of male fastening elements and a second major surface opposite to said first major surface. Each discrete portion is attached to the adhesive layer through the second major surface. A sum of a maximum density of the discrete portions of the backing along the extension of the adhesive layer in the cross-direction and a maximum density of the discrete portions of the backing along the extension of the adhesive layer in the machine direction is at least 0.8 $cm^{-1}$. The assembly can releasably adhere to a fibrous material having a plurality of female fastening elements through a combination of a mechanical and an adhesive bonding mechanism. Methods of making the assembly and disposable absorbent articles containing the assembly are also described.

21 Claims, 5 Drawing Sheets

(51) Int. Cl.
- *A61F 13/20* (2006.01)
- *B31B 1/14* (2006.01)
- *B31B 1/64* (2006.01)
- *B31B 49/04* (2006.01)

(56) References Cited

U.S. PATENT DOCUMENTS

| | | | |
|---|---|---|---|
| 4,067,337 A | 1/1978 | Ness | |
| 4,299,223 A | 11/1981 | Cronkrite | |
| 4,336,804 A | 6/1982 | Roeder | |
| 4,337,772 A | 7/1982 | Roeder | |
| 4,376,440 A | 3/1983 | Whitehead et al. | |
| 4,475,913 A | 10/1984 | Hlaban | |
| 4,568,344 A | 2/1986 | Suzuki | |
| 4,894,060 A | 1/1990 | Nestegard | |
| 4,959,265 A | 9/1990 | Wood et al. | |
| 5,019,065 A | 5/1991 | Scripps | |
| 5,077,870 A | 1/1992 | Melbye et al. | |
| 5,108,384 A | 4/1992 | Goulait | |
| 5,300,058 A | 4/1994 | Goulait et al. | |
| 5,370,634 A | 12/1994 | Ando | |
| 5,507,735 A | 4/1996 | Van Iten et al. | |
| 5,549,591 A | 8/1996 | Landvogt | |
| 5,562,983 A | 10/1996 | Kono | |
| 5,611,790 A | 3/1997 | Osborn, III et al. | |
| 5,676,652 A | 10/1997 | Hunter et al. | |
| 5,679,302 A | 10/1997 | Miller et al. | |
| 5,759,317 A | 6/1998 | Justmann | |
| 5,778,457 A | 7/1998 | Conway | |
| 5,858,515 A * | 1/1999 | Stokes et al. | 428/195.1 |
| 5,897,545 A * | 4/1999 | Kline et al. | 604/386 |
| 5,897,546 A | 4/1999 | Kido et al. | |
| 5,967,009 A * | 10/1999 | Truttmann et al. | 83/52 |
| 6,004,308 A | 12/1999 | Haddock | |
| 6,039,717 A | 3/2000 | Larsson | |
| 6,051,094 A | 4/2000 | Melbye et al. | |
| 6,159,596 A | 12/2000 | Calhoun et al. | |
| 6,393,673 B1 | 5/2002 | Kourtidis et al. | |
| 6,402,730 B1 | 6/2002 | Malowaniec | |
| 6,419,667 B1 | 7/2002 | Avalon et al. | |
| 6,428,525 B1 | 8/2002 | Malowaniec | |
| 6,428,526 B1 | 8/2002 | Heindel et al. | |
| 6,443,932 B1 | 9/2002 | Maggiulli | |
| 6,461,715 B1 | 10/2002 | Guenther | |
| 6,524,294 B1 | 2/2003 | Hilston et al. | |
| 6,554,816 B1 * | 4/2003 | Olson | 604/386 |
| 6,645,190 B1 * | 11/2003 | Olson et al. | 604/389 |
| 6,736,804 B1 * | 5/2004 | Robertson et al. | 604/385.13 |

FOREIGN PATENT DOCUMENTS

| | | |
|---|---|---|
| EP | 0755665 | 1/1997 |
| EP | 0941728 | 9/1999 |
| EP | 0 974 326 A1 | 1/2000 |
| EP | 1002846 | 5/2000 |
| EP | 0734243 | 6/2000 |
| EP | 0700306 | 9/2001 |
| EP | 0755665 B1 * | 2/2002 |
| JP | 11181373 | 7/1999 |
| JP | 2003-126132 | 5/2003 |
| WO | 97/25892 | 7/1997 |
| WO | WO 97/36566 | 10/1997 |
| WO | WO 98/53781 | 12/1998 |
| WO | WO 98/53782 | 12/1998 |
| WO | WO 99/06000 | 2/1999 |
| WO | WO 00/50229 | 8/2000 |
| WO | 01/97738 | 12/2001 |
| WO | WO 03/003962 | 1/2003 |

OTHER PUBLICATIONS

Hartman Brief, dated Apr. 29, 2013, pp. 1-26 (English Translation).
Versuchsn Hartman Brief, dated Apr. 29, 2013, pp. 1-26 achbau zu EP 1 635752 B1, Testing 90° pp. 1-4 and Front-End Munich Scannable and Non Scannable Models, sent on May 2, 2013, 1 page.
Front-End Munich Scannable and Non Scannable Models, sent on May 2, 2013, 2 pages.
ASTM Designation: D3330/D330M-04, Standard Test Method for Peel Adhesion of Pressure-Sensitive Tape, Reapproved 2010, pp. 1-6.
Product Specification 3.116, "production specification FIXIES Ultra Dry", May 24, 1995, 8 pp.
Material Specification M 0.362, WINDELTAPES, Jun. 12, 1995, 7 pp.
Declaration in lieu of Oath by Herr Malowaniec, Mar. 25, 2013, 1 page.
Catalog, Sortimentsliste Konsumgüter, Jul. 1995, pp. 1-24.
Product Listing for Consumer Goods entitled "Sortimentsliste Konsumgüter", Jan. 1996, pp. 1-25.
Production Specification P 3.2100 Molicare (Premium), Oct. 8, 2002, 5 pp.
Production Specification M 2.1001 Tape Molicare, Oct. 2, 2002, 5 pp.
Hartmann Old Molicare 28 Extra Small No. 169213, Nov. 12, 2002, 3 pp.
Oath by Dr. Rüdiger Kesselmeier Apr. 25, 2013, 1 page.
Paul Hartmann AG, dated Feb. 7, 2003, pp. 2-5.

* cited by examiner

FASTENING FILM SYSTEM AND ASSEMBLY COMPRISING A FASTENING FILM SYSTEM AND A SUBSTRATE

FIELD OF THE INVENTION

The present invention relates to an assembly which is suitable for releasably adhering to fibrous materials through a combination of a mechanical and an adhesive bonding mechanism. The present invention furthermore relates to methods of preparing such assemblies and to disposable absorbent articles such as diapers or sanitary napkins employing such assemblies.

BACKGROUND OF THE INVENTION

EP 0,321,232 discloses a disposable absorbent article such as a diaper comprising a pair of tape tabs attached to an end region of said diaper. Each of the tape tabs exhibits on its respective user's end a fastening surface which has one or two exposed rectangular adhesive areas adjacent to a rectangular strip of a hook fastening element. This construction provides a combination of a mechanical and an adhesive closure mechanism when attaching the tape to the landing member thereby securing the diaper to the wearer's body.

EP 0,974,326 also discloses a disposable absorbent article such as a diaper having a pair of tape tabs attached to a first end region of said diaper and a landing member attached to a second end region of said diaper whereby the user's end of the tape tab comprises both mechanical and adhesive fastening means. It is disclosed that the exposed adhesive area of the tape tab may become contaminated with fiber elements when adhering the tape tab to the fibrous landing member. EP '326 discloses a release treatment of the exposed surface of the fibrous landing member in order to minimize or avoid, respectively, damaging of the fibrous landing member and/or contamination of the exposed adhesive area on the tape tabs.

Assemblies providing both a mechanical and an adhesive fastening mechanism are also disclosed in U.S. Pat. No. 6,393,673, U.S. Pat. No. 6,428,525, U.S. Pat. No. 6,402,730, WO 99/06,600 and EP 0,418,951. U.S. Pat. No. '673, for example, describes a mechanical fastening element comprising a multiplicity of flexible hook elements emanating from a backing layer and comprising stems terminating in hook heads wherein the top portions of the hook heads and/or at least part of the interstitial spaces between the stems are coated with a hot-melt pressure sensitive adhesive.

U.S. Pat. No. 4,959,265 discloses a pressure-sensitive adhesive tape fastener comprising a backing having an array of upstanding stems distributed across at least one face, and a pressure-sensitive adhesive layer filling the spaces between the stems where the average thickness of the adhesive layer is less than the average height of the stems. When adhering the pressure-sensitive adhesive tape fastener to a sanitary napkin, the napkin can be releasably attached to an undergarment by allowing the stems to penetrate into openings of the fabric of the undergarment until the pressure-sensitive adhesive becomes releasably bonded to the fabric.

The assemblies disclosed in U.S. Pat. No. 6,393,673, U.S. Pat. No. 6,428,525, U.S. Pat. No. 6,402,730, WO 99/06,600, EP 0,418,951 and U.S. Pat. No. 4,959,265 require in addition to the adhesive layer employed to adhere the mechanical fastening element to a substrate, a further adhesive layer applied to the top portions of the hook heads and/or to at least part of the interstitial spaces between the stems.

Disposable absorbent articles such as sanitary napkins, panty liners and incontinence pads, comprising mechanical and adhesive fastening means arranged separately from each other on different portions of the disposable absorbent article, are known. U.S. Pat. No. 5,676,652 discloses, for example, sanitary napkins comprising adhesive strips on the garment side of the main body of the sanitary napkin and mechanical fasteners on the side wrapping elements. U.S. Pat. No. 5,611,790 discloses sanitary napkins having adhesive fastening means, mechanical fastening means or combinations of adhesive and mechanical fastening means which are arranged separately from each other in patches, for example, on the garment side of the main body of the napkin or on the side wrapping elements.

Sanitary napkins, for example, need to be capable of reliably and releasably adhering to a variety of natural or synthetic fibrous materials such as cotton, silk, nylon, woven, non-woven, knitted and/or microfibrous materials without damaging such materials. These requirements are fulfilled by the sanitary napkins available in the state of the art to an insufficient extent only.

It was therefore an object of the present invention to provide an assembly which is capable of releasably adhering to a variety of fibrous materials through a combination of a mechanical and an adhesive bonding mechanism and which does not exhibit the shortcomings of the fastening surfaces of the state of the art or exhibits them to a lower degree only, respectively. Other objects of the present invention will be readily derivable form the following detailed description.

SUMMARY OF THE INVENTION

The present invention relates to an assembly comprising a substrate bearing an adhesive layer having an extension in a machine direction and an extension in a cross-direction and discrete portions of a backing, each discrete portion having a first major surface bearing a plurality of male fastening elements and a second major surface opposite to said first major surface. Each discrete portion is attached to the adhesive layer through its second major surface. A sum of a maximum density of the discrete portions of the backing along the extension of the adhesive layer in the cross-direction and a maximum density of the discrete portions of the backing along the extension of the adhesive layer in the machine direction is at least $0.8\ cm^{-1}$. The assembly can releasably adheres to a fibrous material having a plurality of female fastening elements through a combination of a mechanical and an adhesive bonding mechanism.

The present invention furthermore relates to a method of preparing an assembly according to the present invention comprising providing the substrate, applying the adhesive layer to an exposed surface of the substrate, providing the discrete portions of the backing having the first major surface bearing the plurality of male fastening elements, and adhering the discrete portions of the backing through the second major surface to the exposed surface of the adhesive layer.

The present invention furthermore relates to a disposable absorbent article such as a sanitary napkin or a diaper comprising a liquid-permeable top sheet, a liquid-impermeable back sheet opposite to said top sheet, a liquid-absorbent core between said top sheet and said back sheet, two longitudinal edges, a first end region and a second end region, the absorbent article further comprising an assembly according to the present invention positioned to secure said disposable absorbent article to at least one of a body or an undergarment of a person.

BRIEF DESCRIPTION OF THE FIGURES

FIG. 3b is a cross-section along the line C-C of the tape tab 27 of the diaper 20b of FIG. 3a.

FIG. 4 is a schematic exploded view of a specific embodiment of a sanitary napkin 20a.

DETAILED DESCRIPTION OF THE INVENTION

Figure 1A:
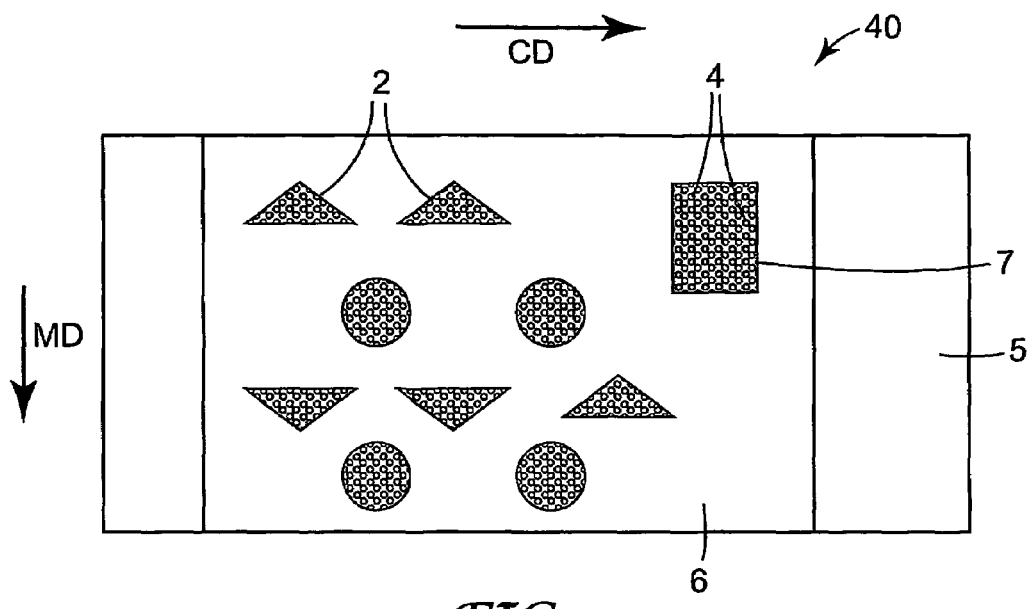
FIG. 1a is a top view of a preferred embodiment of an assembly 40 of the invention.

The present invention relates to an assembly 40 comprising a substrate 5 bearing an adhesive layer 6 on an exposed surface of the substrate 5.

The substrate 5 may be formed by a variety of materials and constructions. In one preferred embodiment the substrate 5 is a disposable absorbent article such as a sanitary napkin 20a. The discrete portions 2 of the backing 7 are preferably attached, through adhesive layer 6, to the back sheet 22 of such sanitary napkin 20a which forms the exposed surface of the substrate 5 and is facing the wearer's garment during use.

In another preferred embodiment the substrate 5 is formed by the support film 34 of a tape tab 27 which may be used in a disposable absorbent article such as a diaper 20b. As is illustrated, for example, in FIG. 3a, the tape tab 27 may form part of the closure system of a diaper 20b comprising a pair of such tape tabs 27 and the landing zone 28 comprising a fibrous material 32. In the specific construction shown in FIG. 3b the support film 34 bears a continuous adhesive layer 6 which is used in the manufacturer's end 27a of the support film 34 to secure the tape tab 27, for example, to the back sheet 22 of the diaper 20b. In the user's end 27b of the support film 34, the discrete portions 2 of the backing 7 are adhered to the adhesive layer 6. The discrete portions 2 of the backing 7, the adhesive layer 6 of the user's end 27b and the support film 34 form the assembly 40.

The support film 34 may comprise only one material and exhibit an essentially uniform construction in the cross-direction, but it may also comprise a sequence of two or more zones in the cross-direction having different properties whereby such zones preferably extend continuously in the machine direction.

Figure 1B:
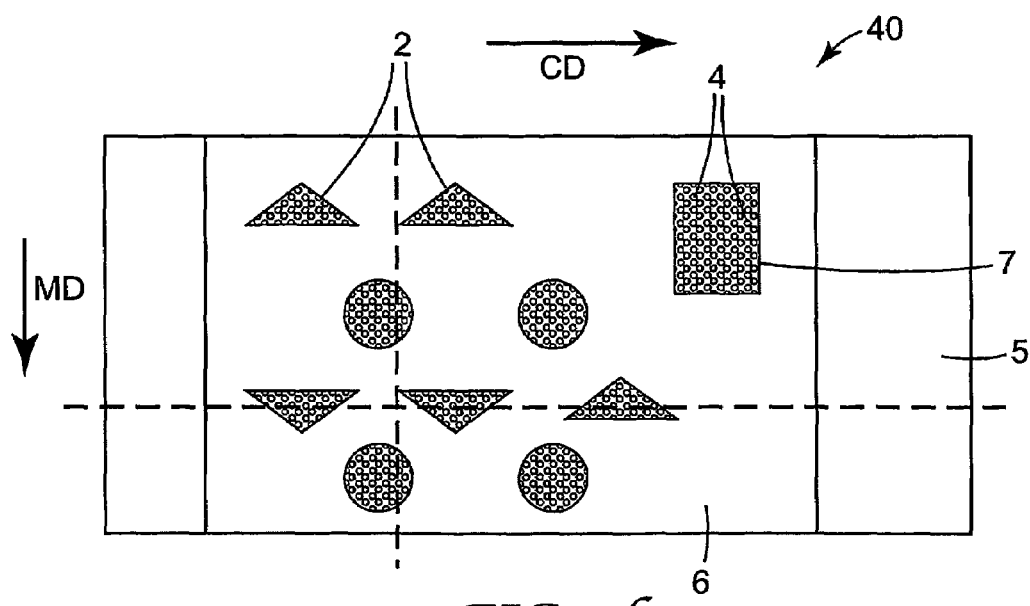
FIG. 1b is a top view of the assembly 40 of FIG. 1a additionally comprising dotted lines in the MD and in the CD used to evaluate the maximum densities of the discrete portions 2 of the backing in such directions.
Figure 2:
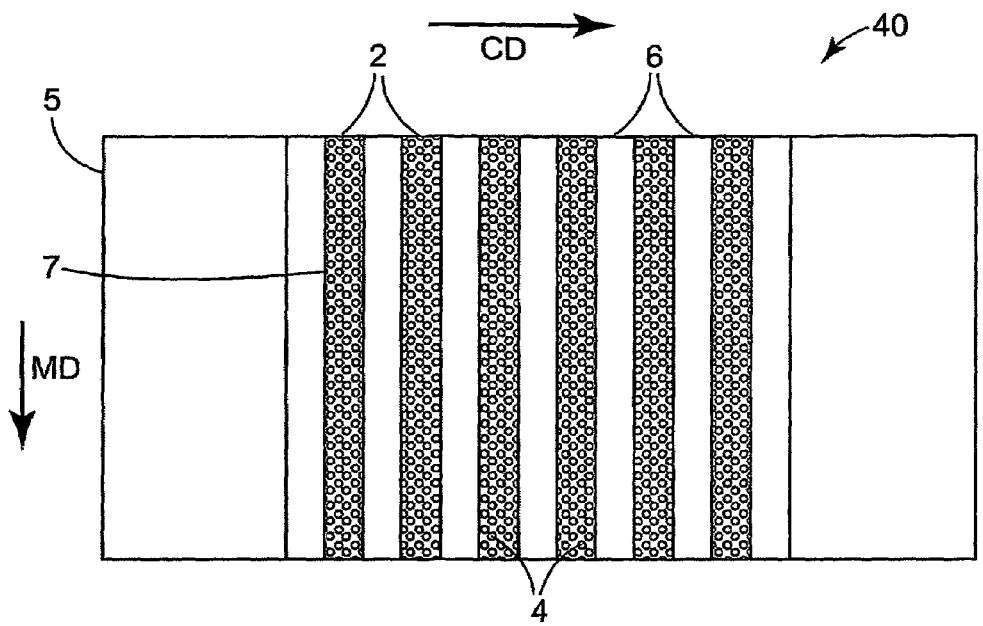
FIG. 2 is a top view of another preferred embodiment of an assembly 40 of the present invention.

The term "machine direction" (MD) as used above and below denotes the direction of the running, continuous web of the substrate 5 or the support film 34 during the manufacturing of the assembly 40. In the embodiment of FIGS. 1a, 1b and 2, for example, the machine direction corresponds to the direction of the lateral edges of the substrate 5. The term "cross-direction" (CD) as used above and below denotes the direction which is essentially normal to the machine direction.

The term "zone" as used above and below refers to a section of the support film 34 in CD exhibiting an essentially uniform construction and/or uniform properties. The different zones can be formed by different materials which are joined to each other, for example, by adhesive means such as pressure-sensitive adhesive means, ultrasonic bonding, thermal bonding, mechanical bonding, stitching or any combination of these bonding methods. It is, however, also possible that different zones are created by "activating" one or more zones of the web. As used above and below, the term "activating" means subjecting the support film 34, for example, to a mechanical, thermal, electrical and/or chemical treatment in order to impart different functionalities to the treated zones of the web.

The different zones of the support film 34 may consist essentially of one material but it is also possible that the zones comprise a sequence of two or more layers of materials and/or exhibit substructures in the direction essential normal to MD and CD.

One or more zones of the support film 34 preferably comprise a carrier film in order to impart structural integrity and/or stiffness to the support film in CD. The carrier film may be selected from a variety of films or sheetings including single- or multilayered films, coextruded films, laterally laminated films or films comprising foam layers. The layers of such films or sheetings may comprise various materials such as, for example, polypropylene, polyvinylchloride, polyethylene terephthalate, polyethylene, polyolefin copolymers or blends of polyolefins such as, for example, a blend of polypropylene, LPDE (low density polyethylene) and/or LLDPE (linear low density polyethylene), textiles, and non-woven and foamed materials. The thickness of the carrier film is preferably between 30 and 500 μm and more preferably between 40 and 150 μm. The base weight of the backing is preferably between 15 and 500 $g/m^2$, more preferably between 20 and 300 $g/m^2$ and especially preferably between 20 and 200 $g/m^2$.

One or more zones of the support film 34 may comprise one or more elastically extensible materials extending in at least one direction when a force is applied and returning to approximately their original dimension after the force is removed.

Elastically extensible materials which are useful in the present invention include materials which preferably are elastically extensible without requiring an activation step. Such materials include elastic, natural or synthetic rubber, rubber foams, elastomeric scrims, woven or non-woven elastomeric webs, elastomeric composites, zero-strain stretch laminates or prestained stretch laminates.

The elastically extensible materials may be made from a group of materials comprising essentially isotropic or essentially anisotropic materials, respectively. Useful elastic materials preferably exhibit an elongation at break as measured according to ASTM D 882 in the preferred direction of stretchability of at least 25% or more and, more preferably, of more than 50% and most preferably of more than 100%.

Preferred essentially isotropically elastic materials include elastomeric polyurethane materials, or natural or synthetic rubber materials such as, for example, ethylene-propylene-diene copolymers (EPDM), styrene-butadiene-styrene block copolymers (SBS) or styrene-(ethylene-butylene)-styrene block copolymers (SEBS). Elastomeric materials of the A-B or A-B-A block copolymer type which are useful in the present invention, include, for example, those described in U.S. Pat. No. 3,265,765, U.S. Pat. No. 3,562,356, U.S. Pat. No. 3,700,633, U.S. Pat. No. 4,116,917 and U.S. Pat. No. 4,156,673. Other elastomeric materials which may be used to form the elastic means include elastomeric polyamide materials and elastomeric polyolefin and polyester materials. Blends of these elastomers with each other or with modifying non-elastomers are also contemplated. For example, up to 50 wt. %, but preferably less than 30 wt. % with respect to the mass of the elastomeric material can be added as stiffening aids such as polyvinylstyrenes, polystyrenes, polyesters, epoxies, polyolefins or coumarone-indene resin. These stiffening aids tend to improve the flexibility of the elastomeric materials.

Preferred elastic materials are commercially available from Exxon Mobil Corp. under the trademark Vector and from Kraton Polymers Comp. under the trademark Kraton.

Additionally or alternatively it is also possible to subject one or more zones of the support film 34 to an activation treatment in order to render such zones elastically extensible and/or to increase such elastic extensibility, respectively. Preferred activation treatments include, for example, MD or CD stretching, ring rolling, embossing, thermoforming, high pressure hydraulic forming or casting. Elastomeric laminates comprising at least one non-elastomeric skin layer and at least one core layer where the laminate is treated to exhibit preferential activation regions and non-preferential activation regions so that the preferential activation regions can be stretched to an elastic state, are disclosed in EP 0,521,388. This elastomeric laminate can be used in the support film 34 of the assembly 40 of the present invention.

The support film 34 may comprise further materials such as, for example, stiffening materials, colored films, printings or registered marks. The support film 34 may also impart further functionalities such as breathability or differential stiffnesses to the assembly 40.

Stiffening materials include, for example, thermally or sonically structured surfaces or additional layers or coatings applied to the support film 34.

The support film 34 preferably has a Gurley stiffness value both in CD and MD as evaluated according to TAPPI Standard Test T 543 om-94, of less than about 1,000 milligrams (mg). The Gurley stiffness both in CD and MD preferably is less than 500 mg and especially preferably less than 200 mg.

The support films 34 suitable for use in the tape tab 27 of a diaper 20b or in a sanitary napkin 20a are described as illustrative examples of substrate 5 only but are not intended to be limiting in any way. The substrate 5 may be formed by any article or construction having an exposed surface capable of bearing adhesive layer 6 of the assembly 40.

The dimensions of the substrate 5 in CD and/or MD may essentially match with the corresponding dimensions of the adhesive layer 6 but it is also possible that the dimensions of the substrate 5 in CD and/or MD differ from and, in particular, exceed the corresponding dimensions of the adhesive layer 6 as is shown, for example, in FIGS. 1 and 2.

The assembly 40 comprises an adhesive layer 6 which is attached to an exposed surface of substrate 5 which may be continuous or discontinuous. The adhesive layer 6 extends on the major surface of the substrate 5 at least to the extent that the discrete portions 2 of the backing 7 are adhered to the substrate and that there is a sufficient additional area of the exposed adhesive layer 6 so that the assembly 40 provides a combination of an adhesive and a mechanical bonding mechanism.

The adhesive of adhesive layer 6 is preferably selected from a group of adhesives having a 90° peel adhesion to a smooth polyethylene test surface as measured according to ASTM D3330F using a roll-down weight of 5,000 g, of between 1 N/inch and 10 N/inch, more preferably of between 1.5 N/inch and 8 N/inch and especially preferably of between 2 N/inch and 8 N/inch If the 90° peel adhesion is less than 1 N/inch, the adhesive bonding mechanism between the fastening film system 1 and a fibrous material 32 brought into contact with it, tends to be undesirably low in many cases. Also, for such low values of 90° peel adhesion, it tends to be difficult to optimize the performance of the assembly 40 with respect to a variety of fibrous materials 32 including both lofty-type fabrics such as cotton based fabrics or more densely woven fabrics such as, for example, nylon based fabrics. If the 90° peel adhesion is higher than 10 N/inch, the adhesive bonding mechanism between the fastening film system 1 and a fibrous material 32 brought into contact with it, tends to be undesirably strong in many cases so that the fibrous material 32 may be damaged. Tacky adhesives which are useful in the present invention preferably include pressure-sensitive adhesives which are selected from a group comprising (meth)acrylate and/or natural or synthetic rubber-based pressure-sensitive adhesives. Rubber-resin additives preferably comprise in addition to the rubber materials one or more tackifying resin in order to render the rubber materials tacky. Preferred examples of rubber-based pressure-sensitive adhesives are the polystyrene-polyisoprene block copolymers tackified with synthetic polyterpene resins. Suitable acrylate-based pressure-sensitive adhesives are disclosed, for example, in U.S. Re 24,906 or U.S. Pat. No. 4,710,536. Suitable synthetic rubber based adhesives are described, for example, in U.S. Pat. No. 5,019,071 and U.S. Pat. No. 3,932,328.

The adhesive layer 6 is applied to an exposed surface of the substrate 5. The adhesive layer 6 may be applied, for example, by coating or spray-coating a solution of the adhesive in an appropriate solvent such as, water, MEK or acetone with subsequent drying. It is also possible to coat a partially cured precursor of the adhesive which preferably is solvent-free, to such exposed surface of the substrate 5 with subsequent curing, optionally in an inert atmosphere of nitrogen and/or argon, for example. The degree of polymerization of the precursor is selected to provide for an appropriate coating viscosity as is disclosed, for example, in U.S. Pat. No. 4,181,752. It is also possible to apply the adhesive layer 6 by hot-melt coating, screenprinting, rotary screenprinting or by lamination of an adhesive layer. The adhesive layer 6 preferably is an unsupported adhesive layer but it can also be formed by one of the two adhesive layers of a double-coated adhesive tape comprising a carrier film bearing two adhesive layers.

The adhesive layer 6 bears discrete portions 2 of a backing 7 comprising on its exposed major surface 3a a plurality of male fastening elements 4 capable of engaging with fibrous materials 32 having a plurality of complementary female fastening elements.

The discrete portions 2 of the backing 7 are adhered to adhesive layer 6 through their major surface 3b which is opposite to their respective exposed major surface 3a.

The discrete portions 2 of the backing may be obtained, for example, by cutting a continuous film of a backing 7 that may be formed by cast molding or extrusion molding. Any cutting operation including rotary knife cutting, punching, die-cutting or laser cutting may be applied. The assembly 40 may comprise discrete portions 2 which were obtained by cutting from one or several continuous backings 7.

Substantially any thermoplastic material suitable for film production can be used to produce the backing 7. Preferred thermoplastic resins include polyesters such as poly(ethylene terepthalate), polyamides such as nylon, poly(styrene-acrylonitrile), poly(acrylonitrile-butadiene-styrene), polyolefins such as polypropylene, and plasticized polyvinylchloride.

The exposed major surface 3a of the backing 7 preferably is essentially flat but it may also exhibit a pattern and the thickness 11 of the backing 7 may, for example, be higher in the center of the discrete portions 2 of the backing 7 as compared to areas at the edges of such discrete portions 2.

The backing 7 may comprise only one material and exhibit an essentially uniform construction in CD, but it may also comprise a sequence of two or more zones in CD having different properties whereby such zones preferably extend continuously in MD. The backing 7 may, for example, be manufactured in a way that layers of different materials are co-extruded or laminated to each other.

The thickness 11 of backing 7 which is essentially flat or the average thickness of a backing 7 which is not essentially flat, respectively, preferably is between 10 μm and 1 mm, more preferably between 12 μm and 800 μm and especially preferably between 15 μm and 750 μm. If the thickness is above 1 mm, the interaction between the exposed adhesive area 6 and a fibrous material 32 being brought into contact with the assembly 40 may be too weak so that no or an insufficient adhesive bonding mechanism is present between the assembly 40 and such fibrous material 32. If the thickness 11 of the backing 7 is less than 10 μm, the adhesive bonding mechanism tends to dominate the interaction between the assembly 40 and such fibrous material 32 to such an extent that especially lofty fibrous materials 32 may be damaged upon separating and rebonding the assembly 40 to the substrate. If the thickness of the backing 7 is less than 10 μm, the mechanical stability of the backing 7 bearing male fastening elements 4 also tends to be too low.

The exposed major surface 3a of the discrete portions of the backing 7 exhibits a plurality of male fastening elements 4. The male fastening elements preferably have a hook shape, and they usually comprise a stem 4a supported by the exposed major surface 3a of the backing 7 and an enlarged section 4b which is positioned at the end of the stem opposite to the exposed major surface 3a of the backing 7. The male fastening elements 4 can also be formed by stems 4a having no enlarged section at the end of the stem 4a opposite to the backing whereby such stems 4a preferably are essentially conical, cylindrical or pyramidal.

The male fastening elements 4 preferably are integral with the exposed major surface 3a of the backing 7 but it is also possible that the male fastening elements 4 are bonded individually or in form of patches each having a support layer bearing one or more male fastening elements 4 to the exposed major surface 3a of the backing 7. Bonding of such individual fastening elements 4 or patches of fastening elements 4, respectively, can be effected, for example, by adhesive bonding, by ultrasonic bonding, by thermal bonding or by stitching. It is disclosed, for example, in WO 00/50,229 to apply discrete hook patches to the exposed surface 3a of a backing 7.

The enlarged section 4b of the male fastening elements 4 may have any shape such as hooks, T's, J's, mushroom-type heads (including concavely curved heads or disc-shaped heads) or any other shape allowing for engagement with complementary female fastening elements.

Male fastening elements 4 suitable in the present invention can be manufactured from a wide range of materials including thermoplastic polymers such as, for example, nylon, polyester, polyolefins or any combination of these. The male fastening elements 4 preferably comprise the material of which the backing 7 is formed.

The dimensions of the individual male fastening elements 4 can be varied widely depending on the application and the structure and loftiness of the complementary female fibrous material 32. When employing the fastening film system 1 of the present invention, for example, in disposable sanitary articles such as incontinence articles, diapers or napkins, the male fastening elements 4 comprising stems 4a and, optionally, an enlarged section 4b at the end of the stem opposite to major surface 3a, preferably are between 40 μm and 2 mm in height above the backing. The stems 4a preferably have a cross-section with a maximum extension of between 10 μm and 250 μm. The ratio of the maximum extension of the enlarged portions 4b of the male fastening elements 4 at the end of the stems 4a opposite to the exposed major surface 3a of the backing 7, over the maximum extension of the cross-sections of the stems 4a preferably is between 1.5:1 and 5:1.

The average surface density of the male fastening elements 4 with respect to the total area of the assembly 40 may vary broadly and preferably is between $10/cm^2$ and $5,000/cm^2$2, more preferably between $20/cm^2$ and $4,000/cm^2$ and especially preferably between $25/cm^2$ and $3,500/cm^2$. If the density of the male fastening elements 4 is less than $10/cm^2$ the strength of the mechanical bonding mechanism between the assembly 40 and a fibrous material 32 brought into contact with the fastening film system 1, tends to be insufficient for practical purposes. If the density of the male fastening elements 4 is above $5,000/cm^2$, the single fastening elements 4 tend to be very small and may not mechanically engage with the fibrous material to a sufficient and/or desirable extent. The manufacture of male fastening elements which are suitable in the present invention is disclosed in the state of the art.

A mushroom-type hook web including a homogenous backing 7 of thermoplastic resin and, integral with the backing 7, an array of upstanding stems 4a projecting from the surface 3a of the backing 7 and having a mushroom head 4b at the end of the stem 4a opposite to the surface of the backing 7, is disclosed, for example, in U.S. Pat. No. 5,077,870. This mushroom-type hook strip can be obtained by feeding the molten thermoplastic resin through a die to a rotating cylindrical mold which has cavities that are negatives of the upstanding stems 4a. The molten resin is injected into the cavities in an excess of an amount that would fill the cavities so that a backing 7 is formed. The resin is solidified and then stripped from the mold as a web that has an array of upstanding stems 4a. The web is then passed between two calendar rolls whereby the roll contacting the tip of the stems 4a is heated to allow for formation of the mushroom heads 4b. U.S. Pat. No. 5,679,302 discloses another mushroom-type hook strip where the enlarged portion 4b at the end of the stems is essentially disc-shaped.

Male fastener webs comprising a homogenous backing 7 and, integral with the backing 7, an array of male fastening elements 4 whereby the enlarged portions 4a have a variety of shapes, is disclosed, for example, in U.S. Pat. No. 4,894,060.

The male fastener webs and the specific geometry of the individual fastening elements 4 disclosed in U.S. Pat. No. 5,077,870, U.S. Pat. No. 5,679,302 and U.S. Pat. No. 4,894,060 are described here only by way of example and are not intended to limit the invention in any way. Other non-limiting examples of suitable male fastener webs are described, for example, in U.S. Pat. No. 4,984,339 and U.S. Pat. No. 5,781,969.

The backing 7 may be subjected to a monoaxial or biaxial stretching prior to cutting of the backing 7 resulting in discrete portions 2 of the backing 7. Biaxial stretching can be applied to the backing 7 subsequently or simultaneously in CD and MD. The term stretch ratio as used above and below denotes the ratio of a linear dimension of a given portion of the stretched backing 7 or the assembly 40, respectively, to the linear dimension of the same portion of the backing 7 or the assembly 40, respectively, prior to stretching. The stretch ratios in MD and CD preferably are independently from each other between 1.1:1 and 8:1 and more preferably between 1.1:1 and 5:1. Biaxial stretching is preferred. Monoaxial stretching or sequential biaxial stretching can be performed, for example, by propelling a continuous web of the backing 7 in the respective direction over rollers of increasing speed.

Simultaneous biaxial stretching can be performed, for example, by using a flat film tenter apparatus as is described, for example, in U.S. Pat. No. 4,675,582, U.S. Pat. No. 4,825,111, U.S. Pat. No. 4,853,602, U.S. Pat. No. 5,036,262, U.S. Pat. No. 5,051,225 and U.S. Pat. No. 5,072,493.

The discrete portions 2 of the backing 7 may exhibit various shapes such as, for example, circular, rectangular, triangular, essentially trapezoid or more complicated regular or irregular shapes. FIG. 1 shows an embodiment of an assembly 40 of the present invention employing discrete portions 2 of the backing 7 having various shapes. FIG. 2 shows a preferred embodiment of an assembly 40 of the present invention comprising rectangular strips 2 of a backing 7 having a plurality of male fastening elements 4. The strips can be obtained, for example, by passing a continuous web of a backing 7 through an appropriately designed rotary knife cutter. The rectangular strips of the backing are arranged on the adhesive layer 6 in a parallel fashion along the machine direction MD and in a distance in the cross-direction CD from each other so that an alternating sequence of parallel strips of exposed adhesive layer 6 and of the discrete portions of the backing 7 is obtained.

It is essential in the present invention that the sum of the maximum densities of the discrete portions 2 of the backing 7 along the extension of the adhesive layer 6 in the cross-direction and in the machine direction, respectively, is at least $0.8\ cm^{-1}$.

In order to determine such maximum density in the CD and MD, the maximum number of discrete portions 2 of the backing is determined as is schematically indicated in FIG. 1b for the assembly 40 of FIG. 1a. When applying a dotted auxiliary line, for example, in the CD and shifting it parallel to the CD along the extension of the fastening film system 1, it is easily established that the maximum number of discrete portions 2 in the CD is 3; this can be seen, for example, when counting the number of discrete portions 2 in the CD along the dotted line included in FIG. 1b. Likewise, when applying a dotted auxiliary line in the MD so that it intersects or touches, respectively, as many discrete portions 2 as possible, it is easily established that the maximum number of discrete portions 2 in the MD is 4 (see FIG. 1b). The dotted lines are imaginary auxiliary lines only and they are included in FIG. 1b for determining the maximum number of discrete portions 2 in the CD and in the MD, respectively.

In this case, the maximum number of discrete portions 2 in the MD is 4 and in the CD 3. The maximum densities in the CD and in the MD are obtained by dividing the numbers by the respective extension of the adhesive layer 6 in the CD and in the MD. These densities are then summed up.

It was found by the present inventors that a well-balanced combination of an adhesive and a mechanical bonding mechanism with respect to a variety of fibrous materials 32 can only be obtained if the sum of the maximum densities of the discrete portions 2 of the backing 7 along the extension of the adhesive layer 6 in the CD and in the MD is at least $0.8\ cm^{-1}$, preferably at least $1.0\ cm^{-1}$, more preferably at least $1.3\ cm^{-1}$ and especially preferably at least $1.5\ cm^{-1}$.

If such sum of the maximum densities of the discrete portions 2 of the backing 7 along the extension of the adhesive layer 6 in the CD and in the MD is less than $0.8\ cm^{-1}$ and, in particular, less than $1.0\ cm^{-1}$, the adhesive bonding mechanism of the assembly 40 towards various fibrous materials 32 as evaluated, for example, by the measurement of the 90° peel adhesion values referred to below, tends to differ distinctly for different fibrous materials 32 so that fibrous materials 32 experiencing a strong adhesive interaction with the respective assembly 40, may be damaged as a result of such strong adhesive interaction. It was also found that the stiffness of the assembly 40 tends to decrease in the CD and/or the MD with an increase of the maximum densities of the discrete portions 2 of the backing 7 along the extension of the adhesive layer 6 in such directions. It was found by the present inventors that sanitary napkins comprising an assembly 40 wherein the maximum densities of the discrete portions 2 of the backing 7 along the extension of the adhesive layer 6 in the CD and in the MD is less than $0.8\ cm^{-1}$ and, in particular, less than $1.0\ cm^{-1}$, tend to exhibit an undesirable stiffness and/or an insufficient wearer's comfort.

If the sum of the maximum densities of discrete portions 2 of the backing 7 along the extension of the adhesive layer 6 in the CD and in the MD is at least $0.8\ cm^{-1}$ and preferably at least $1\ cm^{-1}$, the variation of the adhesive bonding mechanism or the mechanical bonding mechanism, respectively, with respect to various fibrous materials tends to be smaller so that damaging of such fibrous materials 32 is less likely. This is especially advantageous when using an assembly 40 of the present invention in disposable absorbent articles such as disposable sanitary napkins which typically are used with a variety of different fibrous materials 32 such as, for example, different pieces of underwear.

The balance of the adhesive and the mechanical bonding mechanism, respectively, with respect to various fibrous materials 32 can be further optimized by varying the ratio of the sum of the surface areas of the discrete portions 2 of the backing 7 relative to the sum of the exposed adhesive area 6 plus the sum of the surface areas of the discrete portions 2. It was found by the present inventors that this ratio preferably is between 0.15 and 0.8, more preferably between 0.25 and 0.65 and especially preferably between 0.3 and 0.6.

It was also found that assemblies 40 of the present invention having a sum of the maximum densities of the discrete portions 2 of the backing along the extension of the adhesive layer 6 in the CD and in the MD of at least $1\ cm^{-1}$, tend to exhibit a lower values of the adhesive bonding mechanism in comparison to an assembly 40 comprising the same ratio of the sum of the surface areas of the discrete portions 2 of the backing relative to the sum of the exposed adhesive area 6 plus the sum of the surface areas of the discrete portions 2, but a value of the sum of the maximum densities of the discrete portions 2 in the MD and in the CD of less than $1\ cm^{-1}$.

The assembly 40 of the present invention may be obtained by several methods.

In the first step of a preferred method of preparing an assembly 40, an adhesive layer 6 is applied to an exposed surface of the substrate 5. The adhesive layer 6 may be applied, for example, by coating or spray-coating a solution of the adhesive in an appropriate solvent such as, water, MEK or acetone with subsequent drying. It is also possible to coat a partially cured precursor of the adhesive which preferably is solvent-free, to such exposed surface of the substrate 5 with subsequent curing, optionally in an inert atmosphere of nitrogen and/or argon, for example. The degree of polymerization of the precursor is selected to provide for an appropriate coating viscosity as is disclosed, for example, in U.S. Pat. No. 4,181,752. It is also possible to apply the adhesive layer 6 by hot-melt coating, screenprinting, rotary screenprinting or by lamination of an adhesive layer. The adhesive layer 6 preferably is an unsupported adhesive layer but it can also be formed by one of the two adhesive layers of a double-coated adhesive tape comprising a carrier film bearing two adhesive layers.

In the second step of such method of preparing an assembly 40, a plurality of discrete portions 2 of the backing 7 is provided by appropriately cutting a continuous web of the backing 7. Any cutting operation such as rotary knife cutting, punching, laser cutting or die-cutting may be applied.

In the third step of such method, the discrete portions 2 of the backing 7 are bonded through their major surface 3b which is opposite to their exposed major surface 3a comprising a plurality of male fastening elements 4, to the exposed surface of the adhesive layer 6 to provide an assembly 40.

The assemblies 40 of the present invention can preferably be employed in disposable absorbent articles such as, for example, sanitary napkins 20a or diapers 20b.

The term sanitary napkin 20a as used above and below refers to an article which is worn by females adjacent to the pudential region that is intended to absorb and contain the various exudates which are discharged from the body (e.g. blood, menses and urine). The term sanitary napkin 20a is also meant to include light weight incontinence pads for adults. Sanitary napkins 20a typically have a top sheet 21 which provides a liquid pervious body-contacting surface and a back sheet 22 which provides a liquid impervious garment surface. The top sheet 21 and the back sheet 22 sandwich an absorbent core 23 providing the means for absorbing menses and other body fluids. The top sheet 21 is intended to be worn adjacent to the body of the wearer. The back sheet 22 of the sanitary napkin is on the opposite side and is intended to be placed adjacent to the wearer's undergarments when the sanitary napkin 20a is worn.

Constructions of sanitary napkins 20a are described in detail, for example, in U.S. Pat. No. 5,611,790, WO 98/53, 782, U.S. Pat. No. 5,778,457, U.S. Pat. No. 6,039,712, WO 98/53,781, U.S. Pat. No. 4,336,804, U.S. Pat. No. 4,475,913, U.S. Pat. No. 6,443,932 and U.S. Pat. No. 5,507,735.

The present invention, however, is not limited to the particular types or configurations of sanitary napkins 20a described in the above references.

The sanitary napkins 20a according to the present invention differ from prior art constructions in that one or more assemblies 40 are applied to the back sheet 22 and/or other parts of the sanitary napkin 20a, such as the side wrapping elements 30 contacting the wearer's undergarments during use. In a preferred embodiment, an adhesive layer 6 is applied to the back sheet 22 of the sanitary napkin 20a which forms a substrate 5. Subsequently, discrete portions 2 of the backing 7 are adhered to the exposed surface of the adhesive layer 6 through their major surfaces 3b.

The assembly 40 provides an attachment means for securing the sanitary napkin 20a to the wearer's undergarments or panties during use. It was surprisingly found that sanitary napkins 20a according to the present invention can be reliably secured to a variety of undergarments comprising various fibrous materials 32 such as woven, knitted or nonwoven materials comprising, for example, cotton, silk, nylon, polyester, polyolefin such as polypropylene or a mixture of any of the preceding material. The sanitary napkins 20a of the present invention develop a good overall bond strength to a variety of fibrous materials 32 and simultaneously exhibit a good balance of the adhesive and mechanical bonding mechanism so that the sanitary napkin 20a is reliably secured to various types of undergarments without damaging, for example, undergarments with—compared to cotton based materials—a relatively low degree of loftiness by an excessive adhesive bonding strength. Materials with a relatively low degree of loftiness include, for example, silk or nylon based materials whereas cotton based materials typically have a higher degree of loftiness. The loftiness of a fibrous material depends on various parameters including the type and physical characteristics of its fibers and/or filaments and the method of web forming.

The sanitary napkins 20a of the present invention are thus characterized by an increased wearer's comfort. Due to the advantageous balance of adhesive and mechanical bonding properties of the assemblies 40 of the present invention, the sanitary napkins 20a can also be stacked upon each other without requiring, for example, a release-treated interlayer.

The assembly 40 of the present invention can also be used in disposable absorbent incontinence articles such as diapers 20b. Incontinence articles and diapers may have any desired shape such as, for example, a rectangular shape, an I shape, a T shape or an essentially hourglass shape.

Figure 3A:
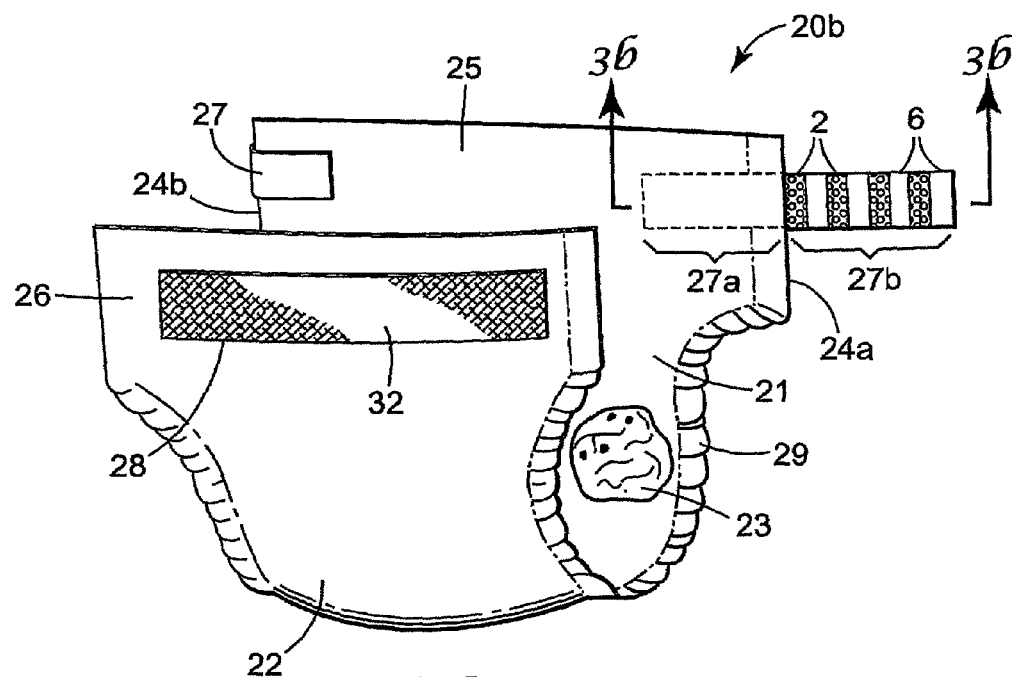
FIG. 3a is a schematic exploded view of a specific embodiment of a diaper 20b.

FIG. 3a is a schematic exploded view of a specific embodiment of a diaper 20b having an essentially hourglass shape. The diaper comprises an absorbent core between a liquid pervious top sheet 21 contacting the wearer's skin, and a liquid impervious back sheet 22 facing outwardly. The diaper 20b has a first end region 25 having two tape tabs 27 arranged at the two longitudinal edges 24a, 24b of the diaper 20b. The tape tabs 27 are secured through their manufacturer's end 27a to the first end region 25. When attaching the diaper 20b to a wearer's body, the user's ends 27b of the tape tabs 27 each comprising an assembly 40 of the present invention are attached to the target area 28 comprising fibrous material 32 which may be arranged on the back sheet 22 of the second end region 26. Examples of loop tapes which may be applied to the target area 28 to provide an exposed fibrous material 32, are disclosed, for example, in EP 0,754,415, EP 0,693,889, EP 0,341,993 and EP 0,539,504.

In an alternative construction, the back sheet 22 comprises a woven or non-woven fibrous layer which is capable of interacting with the user's ends 27b of the tape tabs 27 each comprising a fastening film system 1 or assembly 40 of the present invention so that no separate target area is required. Such back sheets 22 are disclosed, for example, in U.S. Pat. No. 6,190,758 and U.S. Pat. No. 6,075,179.

Figure 3B:
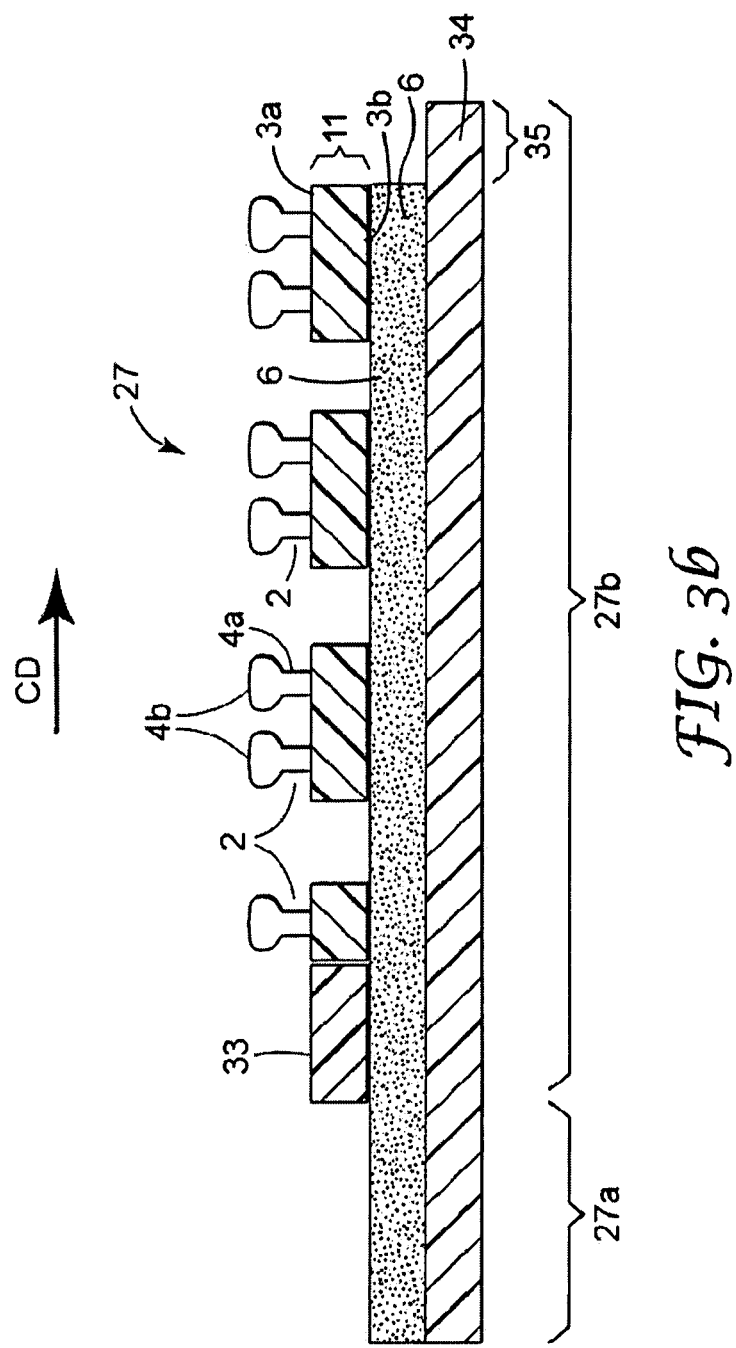
Figure 3C:
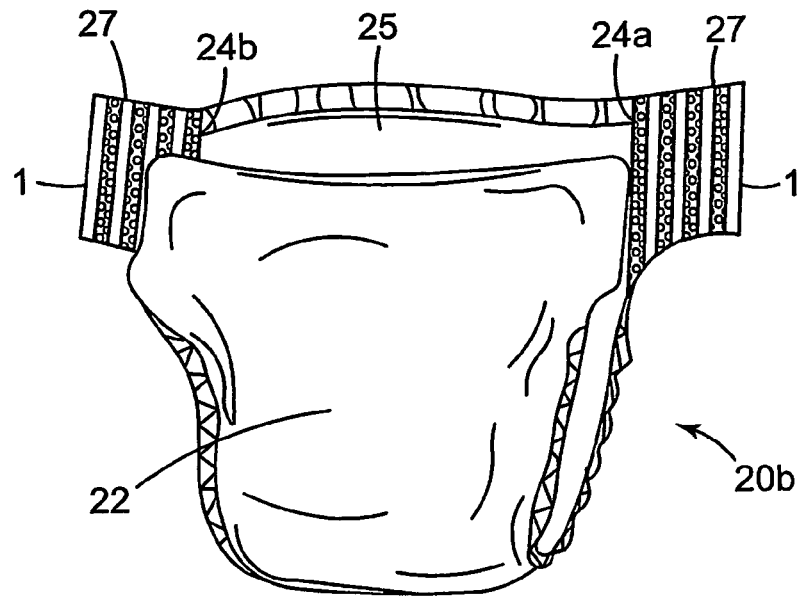
FIG. 3c is a schematic exploded view of another specific embodiment of a diaper 20b.

FIG. 3c is a schematic exploded view of another preferred embodiment of a diaper 20b where a large area tape tab 27 is used comprising a assembly 40 of the present invention. In the construction of FIG. 3c the back sheet 22 is capable of interacting with the assembly 40 via a combination of a mechanical and an adhesive bonding mechanism so that a separate target area 28 is not required.

Figure 3D:
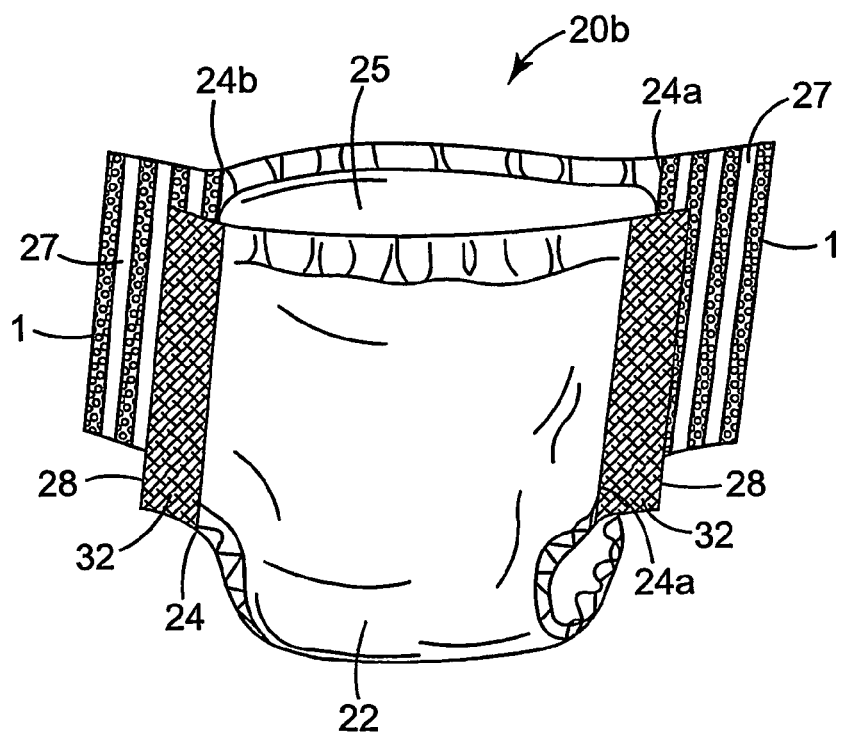
FIG. 3d is a schematic exploded view of another specific embodiment of a diaper 20b.

FIG. 3d shows a schematic exploded view of another specific embodiment of a diaper 20b where a large area tape tab 27 comprising a assembly 40 is used in conjunction with two landing zones 28 comprising a fibrous material 32. The tape tab 27 and the target areas 28 are arranged along the longitudinal edges 24a, 24b of the first and second end region 25, 26.

The tape tab 27 allows to releasably and refastenably attach the diaper 20b around the wearer's body. FIG. 6b shows a schematic cross-section of tape tab 27 comprising a manufacturer's end 27a for securing it to the diaper 20b and a user's end 27b comprising the assembly 40. The user's end is gripped by the user when attaching the diaper 20b to the wearer. The manufacturer's end 27a corresponds to the part of the tape tab 27 which is fixed or secured to the diaper 20b during the manufacture of the diaper 20b; it usually extends from one of the lateral edges (i.e., the edges in cross-direction) oft the tape tab 27 to the longitudinal edges 24a, 24b of the diaper 20b. The user's end 27b corresponds to the part of the tape tab 27 which is not anchored to the diaper 20b during manufacture; it usually corresponds to the part of the tape tab 27 which is different from the manufacturer's end 27a.

During manufacturing or when the diaper 20b is stored prior to use, the user's end 27b of the tape tab 27 is usually folded over onto the top sheet 21 as is shown, for example, for one of the two tape tabs 27 in the diaper 20b of FIG. 3a. It is important during the manufacturing of the diaper 20b that the user's end 27b does not pop open but is releasably secured to the top sheet 21 of the diaper 20b. This so-called "anti-flagging feature" of the tape tab 27 is provided by the exposed surface of the assembly 40 of the tape tab 27 which provides a combination of a mechanical and an adhesive bonding mechanism. When the diaper 20b has been used or soiled, it is typically rolled up after use and discarded whereby it is convenient to secure the diaper 20b in the rolled-up state to avoid spillage of excrements. This so-called "disposal feature" is also provided by the exposed surface of the assembly 40 of the tape tab 27 which provides a combination of a mechanical and an adhesive bonding mechanism.

The tape tab 27 comprises a support film 34 which represents the substrate 5 of the assembly 40. The support film 34 may bear, be bonded to or integrally include, respectively, functional components such as, for example, elastic means, fingerlifts, release tapes to provide a Y-bond between the diaper 20b and the tape tab 27, or cover films 33. The support film 34 and the functional components attached to or incorporated into it, respectively, are selected to impart advantageous properties such as, for example, elasticity, breathability or differential stiffness in machine or cross-direction, respectively, to the tape tab 27. The support film 34 is described above in same detail.

Further details on diapers 20b and their construction are described in literature and may be taken, for example, from U.S. Pat. No. 5,399,219, WO 96/10,382 or EP 0,529,681. Examples for the construction of tape tabs 27 are given, for example, in WO 99/03,437, EP 0,321,232 or U.S. Pat. No. 5,399,219.

The diaper 20b of the present invention differs from prior art constructions in that the user's end 27b of the tape tab 27 comprises an assembly 40. In a preferred embodiment, an adhesive layer 6 is applied to the support film 34 which forms a substrate 5. A plurality of discrete portions 2 of the backing 7 is attached to the adhesive layer through their major surface 3b.

It was found that the tape tab 27 of the present invention has an advantageous combination of an adhesive and mechanical bonding mechanism so that it can be repeatedly opened and re-affixed essentially without damaging the fibrous material 32 arranged, for example, on the landing zone 28 or on the back sheet 22, respectively.

DETAILED DESCRIPTION OF THE FIGURES

FIG. 1a shows the top view of the exposed major surface of an assembly 40 comprising a substrate 5 bearing a continuous adhesive layer 6. A plurality of discrete regions comprising a backing 7 is attached to the adhesive layer 6 through their major surfaces 3b which is opposite to the major surface 3a of the backing 7 bearing a plurality of male fastening elements 4.

FIG. 1b is the top view of FIG. 1a comprising two dotted auxiliary lines used to determine the maximum density of the discrete portions 2 of the backing 7 along the extension of the adhesive layer in the CD and in the MD, respectively.

FIG. 2 shows the top view of the exposed major surface 1a of an assembly 40 comprising a substrate 5 and an adhesive layer 6 bearing rectangular strips of backing 7 having a plurality of male fastening elements 4. The rectangular strips of the backing are arranged on the adhesive layer 6 in a parallel fashion along the machine direction MD and in a distance in the cross-direction CD from each other so that an alternating sequence of parallel strips of exposed adhesive layer 6 and of the discrete portions of the backing 7 is obtained.

FIG. 3a is a schematic exploded view of a disposable diaper 20b comprising a top sheet 21 and a back sheet 22 sandwiching an absorbent core 23. The diaper 20b has a first end region 25 comprising a pair of tape tabs 27 which are secured to the diaper 20b adjacent to longitudinal edges 24a, 24b and which comprise an assembly 40. The diaper has a second end region 26 comprising a fibrous material 32 on the landing zone 28. The tape tabs 27 are secured to the diaper 20b through the manufacturer's end 27a while the user's end 27b is attached to the fibrous material 32 when securing the diaper 20b to the body of a wearer. The diaper 20b comprises an elastic material in the crotch region 29.

FIG. 3b is a cross-section along the line C-C through the tape tab 27 attached to the first end region 25 of the diaper 20b of FIG. 3a. The tape tab 27 comprises a support film 34 bearing adhesive layer 6 which is exposed at the manufacturer's end of the tape tab 27. At the user's end 27b of the tape tab 27, the adhesive layer bears a plurality of discrete strips 2 of the backing 7 each comprising on its exposed major surface 3a a multitude of male fastening elements 4. The portion of the adhesive layer 6 at the user's end 27b of the tape tab 27, the discrete strips 2 of the backing 7 and the support layer 34 form an assembly 40 of the present invention. The tape tab 27 furthermore optionally comprises a cover film 33 covering the exposed part of adhesive layer 6 in the area of the user's end 27b adjacent to the manufacturer's end 27a The outer end of the support film 34 at the user's end exceeds the extension of the backing 7 and the adhesive layer 6 thereby providing a fingerlift 35. The portion of the adhesive layer 6 at the manufacturer's end 27a of the tape tab 27 does not form part of the assembly 40 because it is attached to the back sheet 22 of the diaper 20b and does not interact with the fibrous material 32 on the landing zone 28.

FIG. 3c is a schematic exploded view of another preferred embodiment of a diaper 20b comprising two large area tape tabs 27 which are arranged along the longitudinal edges 24a, 24b of the first end region 25 of the diaper. The tape tabs 27 comprise an assembly 40 of the present invention which interacts with the back sheet 22 of the diaper 20b comprising an exposed fibrous material.

FIG. 3d is a schematic exploded view of another preferred embodiment of a diaper 20b comprising two large area tape tabs 27 each comprising an assembly 40 of the present invention, and two target areas 28 each comprising an exposed fibrous material 32. The tape tabs and the target areas 28, respectively, are arranged along the longitudinal edges 24a, 24b of the diaper 20b.

Figure 4:
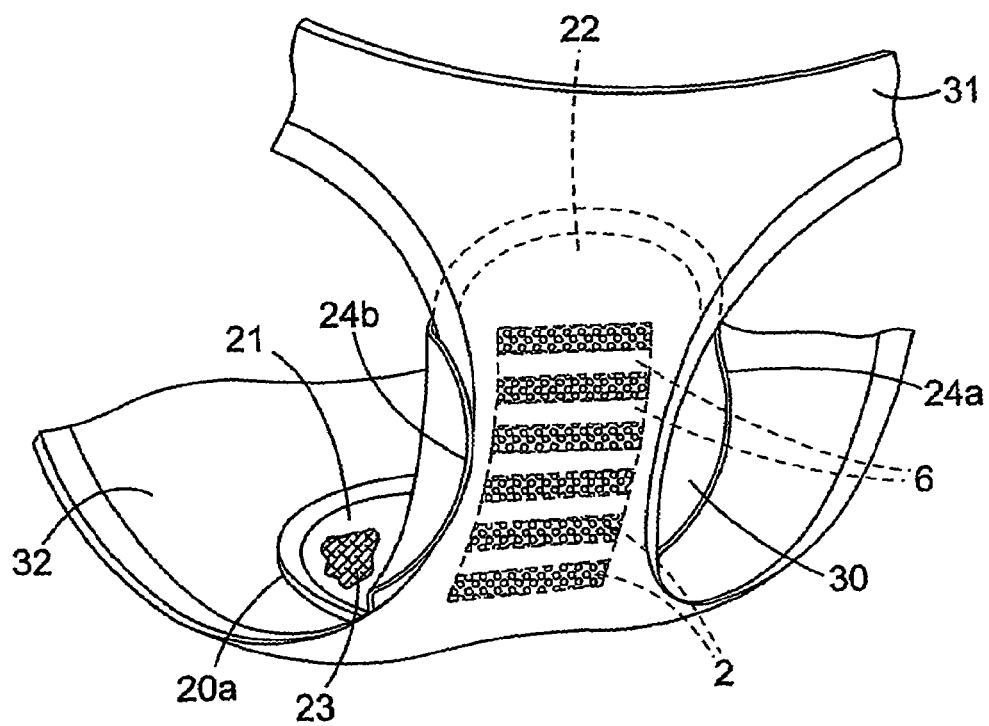

FIG. 4 is a schematic exploded view of a disposable sanitary napkin 20a being attached to a piece of undergarment 31. The napkin 20a has a liquid pervious top sheet 21 and a liquid impervious back sheet 22 sandwiching an absorbent core 23. The napkin 20a furthermore comprises side wrapping elements 30 adjacent to its longitudinal edges 24a, 24b which can be folded over when applying the napkin 20a to the wearer's piece of underwear 31. multitude of discrete portions 2 of the backing is attached to the back sheet 22 of the sanitary napkin 20a so through an adhesive layer 6 so that the major surface 3a of the backing 7 is exposed. The sanitary napkin 20a, the adhesive layer 6 and the discrete portions 2 of the backing 7 form an assembly 40 of the invention.

The present invention will now be further illustrated by the following Examples which are intended to illustrate the invention without limiting it.

TEST METHODS

90° Peel Adhesion

The 90° peel adhesion was measured according to ASTM D 3330 F using a roll-down weight of 5,000 g.

Hang Shear Adhesion

A sample of the fibrous material 32 against which the assembly 40 of the present invention was to be tested, was mounted onto a steel plate with a double-coated adhesive tape. A 40 mm×50 mm piece of the assembly 40 was placed with its exposed surface 3a of the backing 7 comprising the male fastening elements 4, onto the fibrous material 32 and rolled down in one cycle using a roll-down hard rubber roll of 5,000 g at a speed of 30.5 cm/min. The dimensions of the sample of the fibrous material 32 exceeded those of said piece of the assembly 40 so that all of the exposed surface of such piece was contacting the sample of the fibrous material 32. The resulting construction comprising the assembly 40 and the fibrous material substrate 32 was clamped at one end and hung vertically for 15 minutes after which a 100 g weight was attached to the loose bottom end of the resulting construction, generating a shear load at an 180° angle. The time that it took in minutes for the weight to drop at room temperature was recorded as a measure of the hang shear adhesion.

EXAMPLES

Example 1

Discrete portions 2 of a backing 7 were obtained from a mushroom-type hook web which is commercially available under the trade designation 3M Microreplicated Hook CS-600 from 3M Company, St Paul, Minn., USA, by cutting. The portions 2 had the dimension of 5 mm in CD and of 50 mm in MD. The thickness of the hook web including the height of the hook male fastening elements 4 was 396 μm. The average height of the hook male fastening elements 4 was about 310 μm. The hook male fastening elements 4 were integral with the backing 7 of the hook web, and they were distributed essentially homogenously across the surface area of the hook web at a density of 1,626 hooks/inch$^2$. The single hook male fastening elements had a stem 4a with a diameter of about 250 μm and an enlarged, oval-shaped portion 4b at the end of the stems opposite to the backing 7 of the hook web.

The discrete portions 2 of the hook web were then applied onto a PP film substrate 5 bearing a polystyrene-polyisoprene block-copolymer pressure-sensitive adhesive layer with a thickness of about 35 μm in a parallel fashion along the MD and in a distance of 5 mm between adjacent strips in the CD so that an alternating sequence of parallel strips of exposed adhesive layer 6 and of the discrete portions 2 of the hook web was obtained.

The maximum density of the discrete portions 2 of the backing in CD was 4 (=number of the discrete portions 2)/40 mm (=extension of the sample in CD) so that a density of 1 cm$^{-1}$ was obtained. The maximum density in the MD was 1/50 mm=0.2 cm$^{-1}$ so that a sum of the maximum densities of 1.2 cm$^{-1}$ was obtained. The ratio of the exposed area of adhesive 6 over the sum of the areas of the discrete portions 2 and the exposed area of the adhesive 6 was 0.5.

A sample of a 100% cotton fabric (=fibrous material 32) having dimensions exceeding the dimensions of the piece of assembly 40 obtained above, was cut from a piece of plain commercial women's undergarment. The sample was washed once and had a total weight of 195 g/m$^2$ after washing.

Another sample of a nylon/Elasthan™ fabric (96% nylon, 4% Elasthan) having dimensions exceeding the dimensions of the piece of the assembly 40 obtained above, was cut from a piece of a plain commercial women's undergarment The sample was washed once and had a total weight of 170 g/m$^2$ after washing.

The samples of the cotton fabric and the nylon/Elasthan fabric were rolled down on the portion of the assembly 40 as described above to measure the 90° peel adhesion and the hang shear adhesion.

The results are summarized in Table 1 below.

TABLE 1

| Sum of the maximum densities of the discrete portions in the MD and in the CD [cm$^{-1}$] | Average 90° peel adhesion [N/40 mm] | | Hang shear adhesion | |
|---|---|---|---|---|
| | Cotton | Nylon/Elasthan | Cotton | Nylon/Elasthan |
| Ex. 1   1.2 | 1.5 | 6.3 | >1,200 | >1,200 |

We claim:

1. An assembly comprising:
   a substrate bearing an adhesive layer having an extension in a machine direction and an extension in a cross-direction; and
   discrete portions of a backing, each discrete portion having a first major surface bearing a plurality of male fastening elements and a second major surface opposite to said first major surface, and each discrete portion being attached to the adhesive layer through its second major surface,
   wherein a sum of a maximum density of the discrete portions of the backing along the extension of the adhesive layer in the cross-direction and a maximum density of the discrete portions of the backing along the extension of the adhesive layer in the machine direction is at least 0.8 cm$^{-1}$, and wherein the assembly can releasably adheres to a fibrous material having a plurality of female fastening elements through a combination of a mechanical and an adhesive bonding mechanism.

2. The assembly according to claim 1, wherein the maximum density of the discrete portions of the backing along the extension of the adhesive layer in the cross direction and in the machine direction is independently from each other at least 0.5 cm$^{-1}$.

3. The assembly according to claim 1, wherein an average maximum extension of the discrete portions of the backing is at least 1 mm.

4. The assembly according to claim 1, wherein an average distance between the discrete portions of the backing is at least 1 mm.

5. The assembly according to claim 1, wherein an average thickness of the backing is between 10 μm and 1 mm.

6. The assembly according to claim 1, wherein the adhesive layer comprises a pressure-sensitive adhesive.

7. The assembly according to claim 1, wherein the adhesive exhibits a 90° peel adhesion from a smooth polyethylene surface of between 1 N/inch and 10 N/inch.

8. The assembly according to claim 1, wherein an average surface density of the male fastening elements with respect to the surface area of the adhesive layer including the surface area of the discrete portions of the backing is between 10/cm$^2$ and 5,000/cm$^2$.

9. The assembly according to claim 1, wherein the male fastening elements are selected so that they can be releasably engaged with a fibrous material having an area weight of less than 350 g/m$^2$.

10. A method of preparing the assembly according to claim 1, the method comprising;
- providing the substrate;
- applying the adhesive layer to an exposed surface of the substrate;
- providing a multitude of the discrete portions of the backing having the first major surface bearing the plurality of male fastening elements; and
- adhering the discrete portions of the backing through the second major surface to the exposed surface of adhesive layer such that the assembly according to claim 1 is prepared.

11. A disposable absorbent article comprising a liquid-permeable top sheet, a liquid-impermeable back sheet opposite to said top sheet, a liquid-absorbent core between said top sheet and said back sheet, two longitudinal edges, a first end region, second end region, and the assembly according to claim 1 positioned to secure said disposable absorbent article to at least one of a body or an undergarment of a person.

12. The disposable absorbent article according to claim 11, wherein the disposable absorbent article is a disposable diaper comprising tape tabs disposed adjacent each longitudinal edge in the first end region, each of said tape tabs comprising the assembly, said disposable absorbent article further comprising a fibrous material in the second end region capable of mechanically engaging with the male fastening elements of the assembly.

13. The disposable absorbent article according to claim 11, wherein the disposable absorbent article is a disposable sanitary napkin bearing the assembly on the back sheet.

14. An assembly comprising:
- a substrate bearing an adhesive layer having an extension in a machine direction and an extension in a cross-direction; and
- rectangular discrete strips of a backing, each discrete strip having a first major surface bearing a plurality of male fastening elements and a second major surface opposite to said first major surface, said discrete strips being attached to the adhesive layer through their second major surfaces in a parallel fashion along the machine direction and at a distance in the cross-direction from each other such that an alternating sequence of multiple parallel strips of exposed adhesive layer and of the strips of the backing is obtained,
- wherein a sum of a maximum density of the discrete strips of the backing along the extension of the adhesive layer in the cross-direction and a maximum density of the discrete strips of the backing along the extension of the adhesive layer in the machine direction is at least 0.8 $cm^{-1}$, and wherein the assembly can releasably adhere to a fibrous material having a plurality of female fastening elements through a combination of a mechanical and an adhesive bonding mechanism.

15. The assembly according to claim 14, wherein an average maximum extension of the rectangular discrete strips in the cross-direction is at least 1 mm.

16. The assembly according to claim 14, wherein the distance in the cross-direction between the rectangular discrete strips averages at least 1 mm.

17. The assembly according to claim 14, wherein an average thickness of the rectangular discrete strips is between 10 μm and 1 mm.

18. The assembly according to claim 14, wherein a ratio of a sum of surface areas of the rectangular discrete strips to a surface area of the adhesive layer defined by the extension in the machine direction times the extension in the cross-direction is between 0.25 and 0.65.

19. The assembly according to claim 14, wherein the adhesive layer comprises a pressure-sensitive adhesive.

20. A disposable absorbent article comprising a liquid-permeable top sheet, a liquid-impermeable back sheet opposite to said top sheet, a liquid-absorbent core between said top sheet and said back sheet, two longitudinal edges, a first end region, a second end region, and the assembly according to claim 14 positioned to secure said disposable absorbent article to at least one of a body or an undergarment of a person.

21. The assembly according to claim 1, wherein at least one of the discrete portions of the backing is encompassed by the adhesive layer.

\* \* \* \* \*